United States Patent [19]

Kuhlman et al.

[11] 4,363,972
[45] Dec. 14, 1982

[54] WIDE RANGE NOBLE GAS RADIATION MONITOR

[75] Inventors: Harry S. Kuhlman, Vernon; Jeffrey R. Wyvill, III, South Windsor, both of Conn.

[73] Assignee: Combustion Engineering, Inc., Windsor, Conn.

[21] Appl. No.: 139,034

[22] Filed: Apr. 10, 1980

[51] Int. Cl.³ .......................................... G01N 21/01
[52] U.S. Cl. .................................. 250/430; 376/253
[58] Field of Search ............. 250/428, 430, 364, 379, 250/380, 288, 289, 357; 176/19 R, 19 LD

[56] References Cited

U.S. PATENT DOCUMENTS 3,116,210 12/1963 Cochinal et al. ............... 176/19 LD
3,200,041 8/1965 Ralfe et al. ...................... 176/19 LD

FOREIGN PATENT DOCUMENTS 1344367 10/1962 France ......................... 250/430

*Primary Examiner*—Bruce C. Anderson
*Attorney, Agent, or Firm*—Arthur L. Wade

[57] ABSTRACT

A sample chamber has the noble gases of effluent first pumped through it from a nuclear process. A quantifying detector of noble gases in the effluent has a predetermined range. A control system is actuated by the detector at the setpoint of a predetermined count rate to terminate the flow of the effluent from the first pump to the sample chamber. A second pump is connected to the chamber to evacuate the chamber upon termination of the first flow into the chamber. A restricted passage is connected between the chamber and the effluent with which to draw the effluent through the chamber by the second pump for so long as the quantity of noble gases in the effluent is above the predetermined setpoint.

7 Claims, 1 Drawing Figure

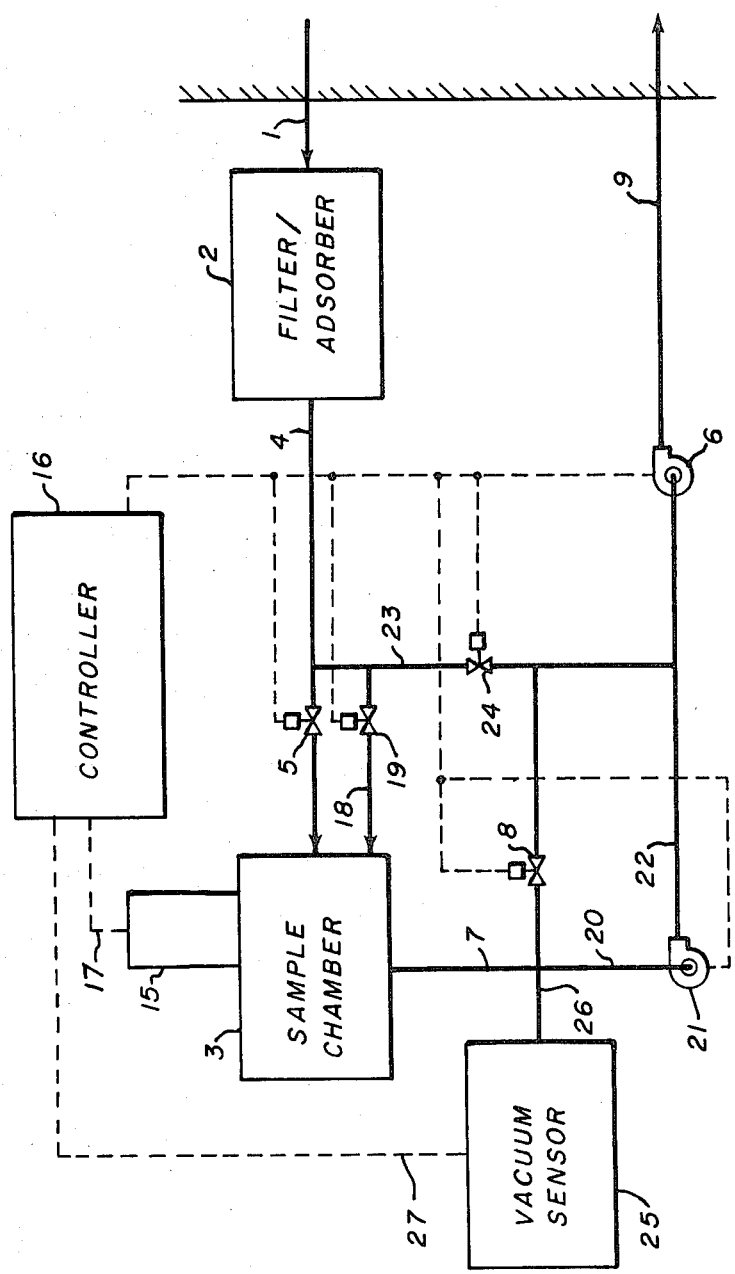

WIDE RANGE NOBLE GAS RADIATION MONITOR

TECHNICAL FIELD

The present invention relates to the detection of noble gases in effluent from a nuclear process by a sample system which maintains the sample within the range of the detector. More particularly, the invention relates to positive evacuation of a gas sample chamber receiving noble gases in effluent from a nuclear process to maintain the sample concentration detection within the range of the detector.

BACKGROUND ART

The attention of the nuclear industry has been internally focused on the inherent dangers of producing power from fissionable products. Although no actual damage to the environment or detrimental effects on personnel have been documented over the many years of nuclear power production, the slightest rumor of mulfunctions of specific nuclear power installations have inflamed the public and caused the over-reaction of governmental regulatory authorities. The industry is expending huge efforts to placate the public and regulatory agencies by reexamining and modifying all its safety precautions subject to criticism.

From the birth of nuclear power generation, the quantity of noble gas emissions from a nuclear process has been of constant concern to the industry. The detectors brought into direct contact with noble gases are fully developed. These detectors are typically of the scintillation type and their count levels have been utilized to indicate and/or control.

The environmentalists have demanded the detectors respond to "As Low As Resaonably Achievable" (ALARA) levels. More specifically, the demand in the past has been for a detector which will include in its range $1 \times 10^{-7}$ $\mu$Ci/cc of noble gases. Presently, the industry is being required to provide the detector with a sample system which will be dependably operative when emissions of noble gases are in the post-accident phase. Therefore, a sample system is demanded which will supply the detector system with a representative sample, both when noble gas emission is very low and yet be able to shift to a mode of operation which allows the detector system to function when the quantity of noble gases surges above the so-called non-accident range during post-accident periods.

It is readily evident that the system must provide a representative sample in both modes of operation. The first mode presents an effluent sample to the sample chamber which is simply drawn off from the normal circuit. The problem descends when noble gases of this sample quantitatively exceed the range of the detector system responsive to the sample in the chamber. The problem is that of quickly replacing the sample in the chamber with one which is in a second mode of reduced concentration in order for the range of variation to be compatible with the detector system.

DISCLOSURE OF THE INVENTION

The present invention contemplates providing a sample system for effluent from a nuclear process wherein the effluent in a first mode passes through a sample chamber whose noble gases are quantitatively detected. The sample of the first mode is continued until the detector count rate reaches a predetermined maximum. The detector establishes a control signal which is applied to terminate the first mode effluent flow to the chamber, evacuate the chamber to a predetermined value of vacuum and connect the effluent into the sample chamber with a predetermined mode of flow rate different from the rate of the first mode to establish a sample concentration in the chamber within the range of the detector. A subsequent predetermined minimum rate will generate a signal to reconnect the sample chamber to the first mode connection and thereby cycle the system back to its first mode of operation.

Other objects, advantages, and features of the invention will become apparent to one skilled in the art upon consideration of the written specification, appended claims and accompanying drawing.

BRIEF DESCRIPTION OF THE DRAWING

The drawing is a schematic of a gas sample system for the noble gases of a nuclear process embodying the present invention.

BEST MODE FOR CARRYING OUT THE INVENTION

General Considerations

The present invention was conceived under the shadow of over-publicized events at Three Mile Island near Harrisburg, Pennsylvania. Motivated by public opinion and administrative pressure, the Nuclear Regulatory Commission (NRC) has now instituted the requirement that all Nuclear Steam Supply System (NSSS) operators monitor gaseous releases to the atmosphere with devices that have a range commensurate with currently postulated "worst case" accidents. Into this breach is cast the present invention embodied in the Wide Range Noble Gas Radiation Monitor. The present invention is embodied in a monitor which meets all the requirements of the "TMI-2Lessons Learned Task Force Status Report and Short-Term Recommendations", NUREG-0578, Section 2.1.8b, Paragraphs 1 and 2, issued by the NRC in July, 1979.

The present invention provides a monitor which operates with a twelve decade activity monitoring range. The monitor functions throughout both non-accident and post-accident conditions.

There is included in the drawing representations of a filter assembly, a detector unit, and a field controller. However, the invention is embodied in the method and apparatus for bringing to the sample chamber that concentration of noble gases which represent both the non-accident mode of operation and the post-accident mode of opertion.

Apparatus Arrangement

No specific source of effluent is disclosed, other than to represent the effluent flowing from the boundary of a nuclear process through conduit 1. Conduit 1 simply connects the embodiment of the invention to the effluent source monitored. The effluent, with its first mode of non-accident concentration of noble gas, is flowed into the system through filter 2. Filter 2 is simply a device which removes particulates and iodine from the effluent to prevent contamination of the sample system.

From the filter 2, the effluent flows into the sample chamber 3 through conduit 4. The flow through conduit 4 into sample chamber 3 is controlled by valve 5. Pump 6 is energized to draw the effluent through conduit 4, through chamber 3 and conduit 7 in the first mode of operation when valves 5 and 8 are open. The discharge of pump 6, through conduit 9, returns to the source from which the effluent originated.

The primary element of detector 15, a scintillation type of radiation detector, is mounted on chamber 3. The count rate signal of detector 15 is established by the concentration of the noble gases to which the primary element of detector 15 is exposed. The manifesting signal output of detector 15 is applied to controller 16 with line 17.

Controller 16 receives manifesting signals and is arranged to establish output signals. These output signals, conventionally in the form of electrical signals, are applied to the valves and pumps of the sample system in which the present invention is embodied.

The post-accident route for the effluent of conduit 1 into sample chamber 3 is provided by conduit 18. The rate of flow of the effluent through conduit 18 into sample chamber 3 is specifically established by the degree of opening through valve 19. When valve 19 controls the rate of effluent flow through chamber 3, the exit from chamber 3 is provided by conduit 20. Pump 21 draws the effluent from chamber 3 through conduit 20 and discharges it through conduit 22 and pump 6.

The system is essentially completed by the provision of conduit 23. The flow through conduit 23 is fixed by valve 24. Valves 24, 8, 19 and 5, along with pumps 21 and 6, are all controlled by signals originating in controller 16. Finally, the vacuum value in chamber 3 is monitored by vacuum sensor 25 through its connection 26 with conduit 7. The vacuum value signal of sensor 25 is transmitted to controller 16 by line 27.

Function of the Apparatus

The function of the apparatus is basically contemplated in two modes. In the first mode of non-accident operation, valve 5 is moved to a full open position in order that the effluent with its first concentration range of noble gases is flowed into sample chamber 3. The signal generated by the detector 15 and controller 16 maintains the valves 5 and 8 open, and valves 19 and 24 shut. Pump 6 is operated and the effluent flows through conduit 4 and valve 5 into sample chamber 3. The detected sample then flows from the chamber 3 through conduit 7, valve 8, pump 6 and conduit 9. During this first mode of operation, the closure of valves 19 and 24 and the inoperativeness of pump 21 precludes any other flow path for the effluent. The first mode of operation contemplates the concentration of the noble gases in the effluent flowed through chamber 3 remaining within the range of detector 15. The problem solved by the invention descends when the concentration of noble gases, resulting from post-accident events, exceeds the range of detector 15. The invention then provides a second mode of operation in combination with the first mode of operation to maintain the detector 15 operative.

The present invention provides a second concentration range of noble gases in the effluent sample chamber to maintain the detector operative within its capability. This sample must be provided to chamber 3 within the shortest possible time. At the same time, the sample must be effectively diluted in its concentration to maintain the detector operative within its first mode range.

Controller 16 has two setpoints near the end of the operable range of detector 15. Assuming the first mode of operation maintains the manifestation of the detector between the two setpoints, post-accident concentrations will cause the setpoint at the upper end of the range to be reached. Detector 15 is arranged to establish an output signal on line 17. When the upper setpoint is reached controller 16 generates signals which will close valves 5 and 8, open valve 24 and energize pump 21. The second mode of operation is thereby initiated.

In review, the second mode of operation terminates the flow through valve 5 and initiates the flow through conduit 18. Additionally, in this second mode, the energization of pump 21 evacuates chamber 3. In other words, the non-accident sample in chamber 3 is positively removed, a vacuum is established in chamber 3, and a predetermined rate of flow into chamber 3 is then flowed through valve 19.

The vacuum value maintained by pump 21 is established by sensing the vacuum value in chamber 3 by vacuum sensor 25. The signal output of sensor 25 on line 27 is placed upon controller 16 and a controller signal output of controller 16 is placed upon valve 19. The regulation of valve 19 thereby maintains a vacuum value on chamber 3 in accordance with the vacuum setpoint of controller 16.

The establishment of the vacuum value in sample chamber 3 and the subsequent introduction of a reduced rate of effluent flow into chamber 3 causes immediate plenary diffusion of the effluent sample throughout chamber 3. Thus is provided the dilution of the concentration of the detected gases necessary to maintain detector 15 operatively within its range. This second mode of operation, and the structure with which it is implemented, constitutes the present invention.

There are features of the structure and its operation ancillary to the invention. It is not necessary to encumber the present disclosure with extensive didactic dissertations explaining all of these auxiliary features. To illustrate with one of these features, it is desirable to maintain a fresh sample of the effluent as close to restricting valve 19 as reasonably possible. Therefore, the valve 19 is provided a connection to conduit 4 as short as possible by conduit 23. The fresh sample from conduit 4 is flowed to valve 19 when valve 24 is opened in the second mode of operation, which arrangement and function shorten the response time of the detector 15 to the second mode of operation.

CONCLUSION

There is more than one valid way to define the invention. From the view-point of its embodiment in apparatus, two conduit circuits can be defined as connected to a source of effluent containing noble gases to be detected. Both of the conduit circuits include the sample chamber where the scintillation type of radiation detector interfaces directly with the effluent flowed through this common chamber. The flow in the first of the conduit circuits is controlled by the on/off valve 5 and the flow in the second of the conduit circuits is controlled by the regulating valve 19. The operation of these valves determine into which of the two conduit circuits the effluent sample flows.

After detection in sample chamber 3 the effluent sample exits through conduit 7. The first circuit is completed through valve 8, the lower part of conduit 23 and pump 6 which discharges through conduit 9. The first mode of operation contemplates the flow of effluent through this first conduit circuit as powered by pump 6. Of course, it is expected that the non-accident range of noble gas in the effluent will be detected in sample chamber 3 when it is passed through this first conduit circuit.

The second conduit circuit is regarded as extending from its connection with conduit 4, parallel to that part of conduit 4 in which valve 5 is mounted. In any event, it is clear that conduit 18 provides an alternate route for the effluent sample into chamber 3. The exit from chamber 3 for the second conduit circuit also includes conduit 7, and then is completed through conduit 20, second pump 21, conduit 22, first pump 6 and conduit 9. In broad sweeping terms, the invention contemplates control of valves 5 and 19 to divert the effluent sample through the restriction established through valve 19, drawn by actuation of second pump 21.

When the second mode of operation occurs at the predetermined end point of the range of detector 15, second pump 21 is actuated through controller 16 and quickly evacuates the first mode sample from chamber 3 and then draws into chamber 3 the effluent sample through valve 19 at the reduced flow rate.

A predetermined value of vacuum is established in chamber 3 by sensor 25 controlling the setting of valve 19 through controller 16. The restricted sample flow into chamber 3 is diffused through the volume of chamber 3 and, in effect, provides the detector with a dilution of the effluent sample.

This diluted sample is detected by 15. The detector, of course, is calibrated to manifest the quantity of noble gases in both the diluted and undiluted effluent sample. The result is an extension of the range of detector 15 as the quantity of noble gases in the effluent shifts from a predetermined non-accident range of values to a predetermined post-accident range of values.

As stated supra, there is more than one way to define the invention disclosed. Regarding the invention as embodied in the method of operation sample chamber 3, the effluent sample containing the noble gases of a nuclear process is passed through the sample chamber 3 in two alternate modes.

In the first mode, the effluent sample is passed through chamber 3 at a first rate of flow. The first conduit circuit containing an on/off valve 5 is the preferred embodiment with which to carry out this process. When the quantity of noble gases in the effluent sample reaches a predetermined value, the effluent sample is isolated from the first conduit circuit by closing valve 5 and alternatively flowed into sample chamber 3 by the second conduit circuit passing through the restriction of valve 19. With the first mode sample evacuated from chamber 3, the second mode sample passed through the restriction of valve 19, completely diffuses in chamber 3 as it enters at the reduced rate.

The invention, from the standpoint of calling for the operation of sample chamber 3, is defined by the foregoing steps. The effluent sample is flowed at two different rates through the chamber while the chamber is held at a predetermined value of vacuum during the reduced flow rate.

From the foregoing, it will be seen that this invention is one well adapted to attain all of the ends and objects hereinabove set forth, together with other advantages which are obvious and inherent to the method and apparatus.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawing is to be interpreted in an illustrative and not in a limiting sense.

The invention, having been described, what is claimed is:

1. A sample and detection system for noble gas emission of a nuclear process, including,
    a sample chamber adapted to receive effluent containing a quantity of noble gases to be detected and manifested,
    a first conduit circuit including the sample chamber flowing the effluent containing a quantity of noble gases to be detected and manifested,
    a first pump connected to the first conduit circuit energized to draw the effluent sample through the chamber,
    a second conduit circuit including the sample chamber flowing the effluent containing the noble gases to be detected and manifested,
    a second pump connected to the second conduit circuit energized to draw the effluent sample through the chamber,
    a detector of noble gases connected to the chamber and establishing an output signal in accordance with the count rate of the detector,
    a first valve in the first conduit circuit upstream of of the chamber,
    a second valve in the second conduit circuit upstream of the chamber,
    and a controller connected to receive the output signal of the detector and the first and second valves and the second pump to close the first valve and open the second valve a predetermined degree and actuate the second pump,
    whereby the controller opens the first valve during the time the detector responds to a first range of noble gases in the effluent passed through the chamber and closes the first valve and opens the second valve and energizes the second pump when the detector responds to a second range of noble gas quantities in the effluent greater than the first range.

2. The system of claim 1, including,
    a vacuum value detector connected to the second conduit circuit generating an output signal to the controller to establish the degree of opening of the second valve which will establish a predetermined vacuum value in the sample chamber when the second pump is energized.

3. A system for supplying effluent containing noble gases of a nuclear process at two different concentrations for detection and manifestation, including,
    a source of effluent containing noble gases whose quantity is to be detected
    a first conduit in which the effluent containing noble gases is flowed,
    a sample chamber adapted to be connected to the first conduit,
    a second conduit connecting the first conduit to the sample chamber,
    an on/off valve in the second conduit for controlling the flow of the effluent from the first conduit into the chamber,
    a third conduit connecting the first conduit to the sample chamber,
    a regulating valve in the third conduit for establishing the rate of flow of the effluent from the first conduit into the chamber, a detector of vacuum values connected to the chamber sensitive to the vacuum valve in the chamber when the effluent flows through the third conduit, a detector of noble gases in the effluent connected to the chamber and establishing an output signal representative of quantity of noble gases in the effluent within the chamber.

a controller connected to receive the output signals of the vacuum value detector and the noble gas detector and establishing output control signals to the on/off valves which open the on/off valve and close the regulating valve during a first range of noble gas quantities in the effluent and close the on/off valve and control the opening of the regulating valve by the output signal of the vacuum value detector during a second range of noble gas quantities in the effluent.

4. The system of claim 3 in which the means for flowing the effluent through the second conduit and the chamber is a first pump connected to the chamber, and the means for flowing the effluent through the third conduit and the chamber is a second pump whose vacuum values established in the chamber are sensed by a vacuum value detector.

5. The process for providing a sample of gas containing noble gases generated by a nuclear process, including, drawing gases containing noble gases of nuclear generation into a circuit, first connecting the circuit to a sample chamber, detecting the quantity of noble gases in the sample flowed through the chamber at a first predetermined rate, determining when the proportion of noble gases in the chamber increases to a predetermined maximum value.

establishing a signal by the predetermined maximum value of the detected noble gases in the sample, utilizing the signal to terminate the flow of sample at the rate into the chamber, utilizing the signal to flow the sample into the chamber by a second predetermined rate, detecting the quantity of noble gases in the sample flowed through the chamber at the second predetermined rate, and whereby the detection of the noble gases in the sample passing through the chamber are maintained within a common detecting range.

6. The process of claim 5, in which, the vacuum is maintained in the chamber following its evacuation of the sample flowed into the chamber at the first rate by continually sensing the vacuum value directly, and utilizing the sensed value to modify the second rate of flow of the sample into the chamber, 7. The method of operating a sample chamber in which the noble gases in effluent from a nuclear process are detected, including, a first mode of operation during which; the effluent containing noble gases to be detected is passed through the chamber at a first rate of flow, and the noble gases in the effluent are detected over a first quantity range;

a second mode of operation during which, the flow of effluent into the chamber is terminated when a predetermined quantity of noble gases in the effluent is detected in the chamber, the chamber is connected to a source of vacuum to evacuate the chamber to a predetermined vacuum value, the effluent containing the noble gases to be detected is passed through the chamber at a second rate of flow, and the noble gases in the effluent of the second flow rate are detected over a second quantity range.

* * * * *